United States Patent [19]

Newell

[11] Patent Number: 5,517,999
[45] Date of Patent: May 21, 1996

[54] AUTOMATIC BLOOD PRESSURE MONITOR WITH A DUAL-SPEED CONTROL CIRCUIT FOR THE DC INFLATION PUMP MOTOR

[75] Inventor: Scott Newell, Ipswich, Mass.

[73] Assignee: Siemens Medical Systems, Inc., Iselin, N.J.

[21] Appl. No.: 249,588

[22] Filed: May 26, 1994

[51] Int. Cl.⁶ .................................................. A61B 5/021
[52] U.S. Cl. ................................................... 128/677
[58] Field of Search ..................... 128/672, 677–686; 417/28, 45, 302

[56] References Cited

U.S. PATENT DOCUMENTS 4,178,918  12/1979  Cornwell .......................... 128/682
4,800,892  1/1989   Perry et al. ........................ 128/677
4,969,466  11/1990  Brooks .......................... 128/677 X
5,240,008  8/1993   Newell .......................... 128/677 X

*Primary Examiner*—Angela D. Sykes
*Attorney, Agent, or Firm*—Mark H. Jay; Lawrence C. Edelman

[57] ABSTRACT

An automatic blood pressure monitor has a dual-speed control circuit which is used to control the speed of a DC motor that powers the inflation cuff. The control circuit limits the motor current, permitting operation from a limited power source (such as a battery). The control circuit also includes structure for electrically braking the motor; the motor is braked after a time delay which commences after motor power is cut off.

8 Claims, 3 Drawing Sheets

AUTOMATIC BLOOD PRESSURE MONITOR WITH A DUAL-SPEED CONTROL CIRCUIT FOR THE DC INFLATION PUMP MOTOR

BACKGROUND OF THE INVENTION

The invention relates to automatic blood pressure monitors, and more particularly relates to the inflation pump used to inflate the inflation cuff. In its most immediate sense, the invention relates to circuitry which is used to control a DC motor that powers the inflation pump, and which is capable of properly inflating even the small inflation cuffs used for neonates.

In an automatic blood pressure monitor, an inflation cuff is slipped onto e.g. the patient's upper arm and inflated to a pressure which exceeds the patient's systolic pressure. This collapses the main artery in the patient's arm and cuts off blood flow to the lower arm. Then, the inflation cuff is slowly deflated while the pressure inside the cuff is monitored using a pressure transducer. The patient's systolic and diastolic pressures can then be determined by monitoring the output of the pressure transducer (which responds to variations in cuff pressure caused by the patient's pulse) and correlating that output with the pressure within the cuff.

While the cuff must be inflated to an inflation pressure which exceeds the systolic pressure, the excess should not be great because this unnecessarily prolongs the measurement process and also unnecessarily stresses the patient's arm. To accurately control the inflation process and cease cuff inflation at an appropriate pressure, it is advantageous to have the pump deliver air at more than one rate. This is because automatic blood pressure monitors are used with cuffs that vary greatly in size; a large cuff may be large enough to encompass the human thigh, while a neonatal cuff may be so small as to just fit over an adult's little finger. The rate of inflation of a neonatal cuff should be only a small fraction—perhaps ⅕—of the rate of inflation of a large cuff.

In the past, as is disclosed in commonly-owned U.S. Pat. No. 5,240,008, a pump powered by a DC motor has been used to inflate the cuff, and the rate of air delivery has been adjusted by using valves to vary the supply of intake air to the pump. Such an adjustment scheme requires the use of relatively expensive electromechanical components. It would be advantageous to eliminate the use of such components if possible and to vary the rate of air delivery by appropriately controlling the speed of the pump motor.

It would be advantageous to provide an automatic blood pressure monitor which varied the rate of air delivery from the pump by controlling the speed of the DC pump motor using a multi-speed control circuit, which control circuit would properly regulate the air output of the pump at a high volume rate and at a low volume rate which is small as compared with the high volume rate.

One object of the invention is to provide an automatic blood pressure monitor which will pump air into the cuff both at a high volume rate and at a low volume rate which is small as compared with the high volume rate, and which operates by varying the speed of a DC motor used to drive the pump.

Another object is, in general, to improve on known automatic blood pressure monitors of this general type.

In accordance with the invention, the air pump is of a type (e.g. a triple-diaphragm type) which produces an acceptably low pressure ripple at low speeds of the motor shaft. In further accordance with the invention, use is made of a well-known characteristic of a DC motor, namely that the motor winding of a DC motor generates an EMF (a voltage) which is directly proportional to the speed of the motor. In accordance with the invention, this EMF is determined and a feedback loop is used to maintain this EMF at a constant value to maintain the motor speed at a highly constant rate in spite of variations in load. In further accordance with the invention, this feedback loop is operated in one of two modes. In the first mode, a high volume rate mode, the DC pump motor is operated at a high speed. In the second mode, a low volume rate mode, the DC pump motor is operated at a low speed which is small as compared with the high speed.

Advantageously, and in accordance with the preferred embodiment, there is a second feedback loop which is used to control motor current. This prevents excessive current consumption when the motor is started.

Further advantageously, and in further accordance with the preferred embodiment of the invention, the high speed mode causes the motor to be operated at its maximum speed.

Further advantageously, and in accordance with the preferred embodiment, when the motor is turned off, it is first disconnected from power and later dynamically braked by shunting through a low resistance; this stops the motor sooner and thus reduces the cuff pressure overshoot from that which existed when the pump was switched off.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
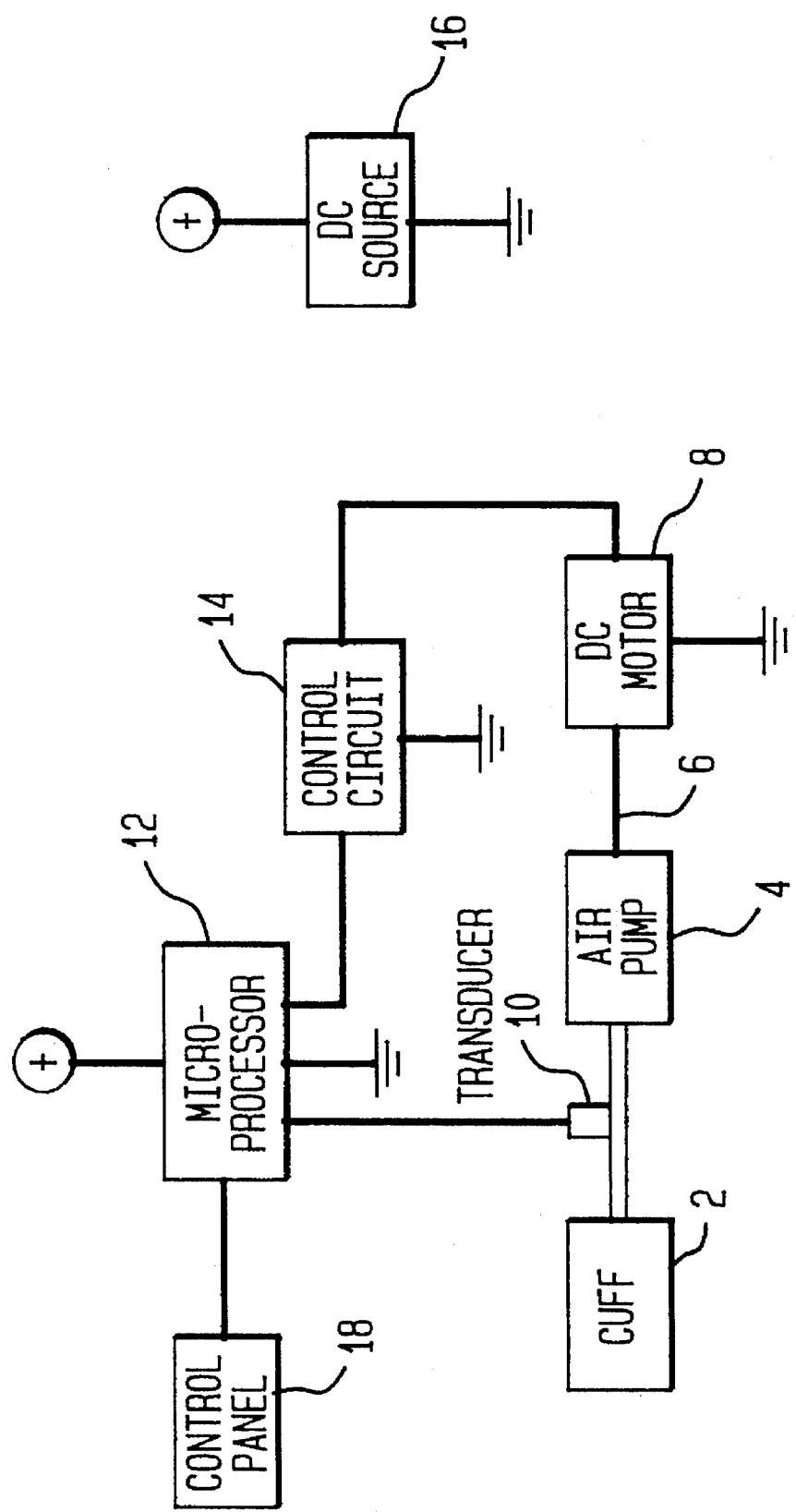
FIG. 1 is a block diagram of a portable battery-powered automatic blood pressure monitor in accordance with the preferred embodiment of the invention.

In an automatic blood pressure monitor, an inflatable cuff 2 is placed upon e.g. a patient's upper arm (not shown) and inflated with a fluid (advantageously, air). The inflation takes place because of the action of an air pump 4 which is driven by the shaft 6 of a DC motor 8; in this example, the pump 4 is of the triple-diaphragm type and therefore delivers three pulses of air for each revolution of the shaft 6, but this is not necessary to the practice of the invention. It is only necessary that the pump 4 produce an acceptable pressure ripple at low speeds.

A pressure transducer 10 communicates with the interior of the cuff 2 and is connected to a microprocessor 12, which in turn is connected to a control circuit 14 that will be described in more detail below. The control circuit 14 starts, stops and controls the speed of the motor 8 according to commands from the microprocessor 12, and the entire unit is powered by a DC source 16 (which may be, but need not be, a battery). A control panel 18 is connected to the microprocessor 12, to permit a technician (not shown) to input instructions.

Figure 2:
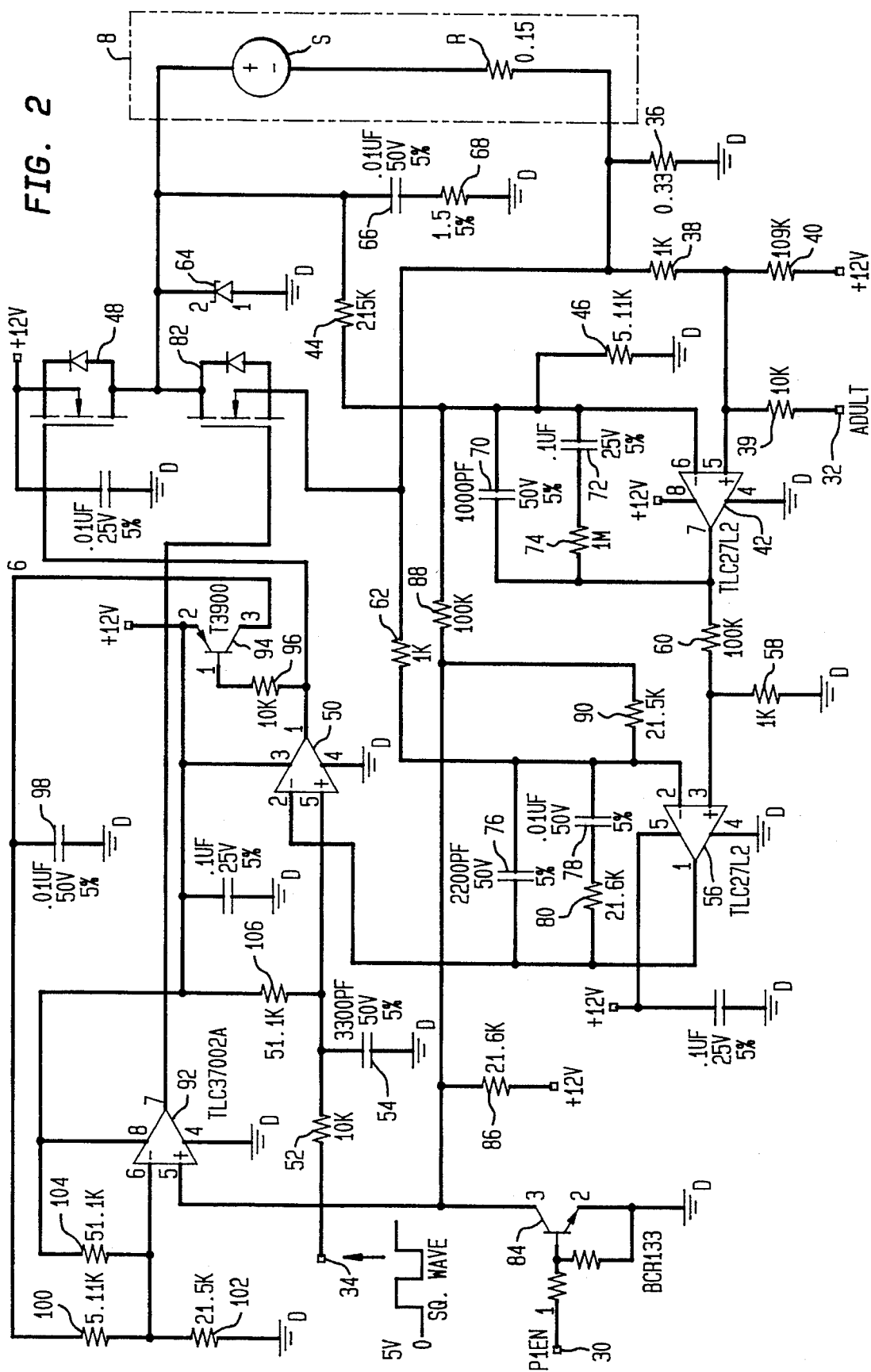
FIG. 2 is a schematic diagram of a circuit in accordance with the preferred embodiment of the invention.

The operation of the control circuit 14 will now be further described with reference to FIG. 2. It will be understood that the details of how the cuff 2 is inflated and deflated are not described herein; the present invention does not reside in the particular way that the cuff 2 is inflated and deflated.

The control circuit 14 is shown connected to the DC motor 8 and controls the operation of the motor 8 as described below. There are two control inputs to the control circuit 14; an "on-off" input 30, and a "mode" input 32. To turn the motor 8 on, a logically high (+5 volt) signal is directed to input 30; a logically low (0 volt) signal at input 30 turns the motor 8 off. (As stated above, the conditions under which the motor 8 is to be turned on and off are not stated here because this is beyond the scope of the present invention.) To control the speed of the motor 8 at a high speed for use on "adults" a logically high signal is impressed upon input 32; to control the speed of the motor 8 at a low speed (in this example, about 20% of the high speed) for use on neonates, a logically low signal is impressed upon input 32. Additionally, a clock input 34 accepts a 25 kHz 5 volt clock signal; a pulse-modulated version of this clock signal is used as described below to vary the speed of the motor 8.

As will become clear below, the preferred embodiment of the invention utilizes two feedback loops to regulate the voltage across the motor 8. The first feedback loop controls the speed of the motor 8 so that it neither slows down when the load on the motor 8 increases nor speeds up when the load on the motor 8 decreases. (At low motor speeds, and for constant voltage across the motor 8, the motor speed is primarily determined by the load on the motor 8.) The second feedback loop—which takes as an input the error signal generated by the first feedback loop—controls the current through the motor 8. Since the command to the second feedback loop is limited in value, the motor current is limited by the second feedback loop. This limits the drain on the source 16 and prevents current surges through the motor 8 when the motor 8 is first turned on. In the following description, the first feedback loop will be described first and the second feedback loop will be described afterward.

Operation of the first feedback loop (which involves the operational amplifier 42): It is known from DC motor theory that a DC motor (e.g. motor 8) can be accurately modeled by a variable EMF source S which is in series with a constant resistance R. When in operation, the motor produces a mechanical torque which is proportional to motor current, the source S produces EMF which is directly proportional to the speed of the motor, and there is an internal voltage drop across the windings within the motor (i.e. across R) which is proportional to motor current. It follows from this theory that the speed of a DC motor can be determined electrically by determining the EMF produced by the motor winding. In known speed control circuits for use with DC motors, this determination is made by subtracting, from the total voltage across the motor, the internal voltage drop which occurs across the motor resistance. In such known speed control circuits, speed control is accomplished by maintaining the resulting difference signal at a predetermined value by using a feedback loop. This control principle—in a modified form—is utilized in the first feedback loop to regulate the speed of the motor 8. As will be seen below, in accordance with the preferred embodiment of the invention, a first feedback loop is established which equalizes two voltages: a first voltage, which represents the sum of a speed-setting command voltage C and the internal voltage drop D across the motor windings, and a second voltage which equals the total voltage across the motor. Since the above-stated theory holds that the second voltage equals the sum of the voltage drop D and the EMF generated by motor operation, we have $$C+D=D+EMF$$

so that in the preferred embodiment of the invention, the first feedback loop causes EMF to be held constant and equal to the command voltage C. In this way, the first feedback loop controls the speed of the motor 8.

To implement this motor speed control scheme, a small resistor 36 is placed between the motor 8 and ground. Additionally, a voltage divider formed of resistors 38 and 40 is placed in series between the positive supply and the resistor 36.

Let it be assumed that the control circuit 14 is to be operated in the "neonatal" mode, i.e. that no logically high signal is input to input 32. In this instance, the voltage at the non-inverting input of an operational amplifier 42 is the sum of two voltages; a first command voltage C which results from voltage division of the positive supply in the divider formed by the resistors 40 and 38 (in the preferred embodiment, resistor 40 is 196 K$\Omega$, resistor 38 is 1 k$\Omega$ and resistor 36 is 0.33$\Omega$, so resistor 36 may be neglected in this computation) and the second voltage is the voltage across the resistor 36 (which voltage, at maximum, is on the order of 100 mV). It may be understood that since the current passing through the resistor 38 is very small, the voltage across the resistor 36 reflects only the current through the motor 8, and therefore reflects the voltage drop across the resistance R of the winding of the motor 8. Consequently, the voltage at the non-inverting input of the operational amplifier 42 reflects the sum of a) the command voltage C which is determined by the resistors 38 and 40 and b) the voltage drop across the resistance R of the winding of the motor 8. (The resistor 39, which connects the input 32 with the non-inverting input of the operational amplifier 42, has only a negligible effect on the circuit.) Additionally, a voltage divider composed of resistors 44 and 46 is connected between the positive side of the motor 8 and ground, and the tap of this voltage divider is connected to the inverting input of the operational amplifier 42. It may therefore be understood that the voltage at the inverting input of the operational amplifier 42 reflects the total voltage across the motor 8. (The resistor 88 has only a negligible effect on the voltage at the inverting input of the operational amplifier 42.)

The operational amplifier 42 is part of a first feedback loop, which is so connected as to equalize the voltages at the inputs of the operational amplifier 42. Thus, the total voltage across the motor 8 is maintained equal to the sum of the command voltage C and the internal voltage drop across the windings of the motor 8, whereby the EMF generated by the motor 8 is held constant at the command voltage C.

The operation of the referenced first feedback loop will now be described, assuming that a logically high signal is applied to the input 30, i.e. that the motor 8 is to be turned on. A P-channel FET 48 is placed in series between the +12 volt supply and the motor 8. Thus, the duty cycle of the FET 48 determines the average value of the voltage across the motor 8 and determines the speed of the motor 8. In accordance with the preferred embodiment of the invention, the duty cycle of the FET 48 is controlled by producing a pulse-width modulated signal at the output of a comparator 50 and applying that signal to the gate of the FET 48.

Figure 3:
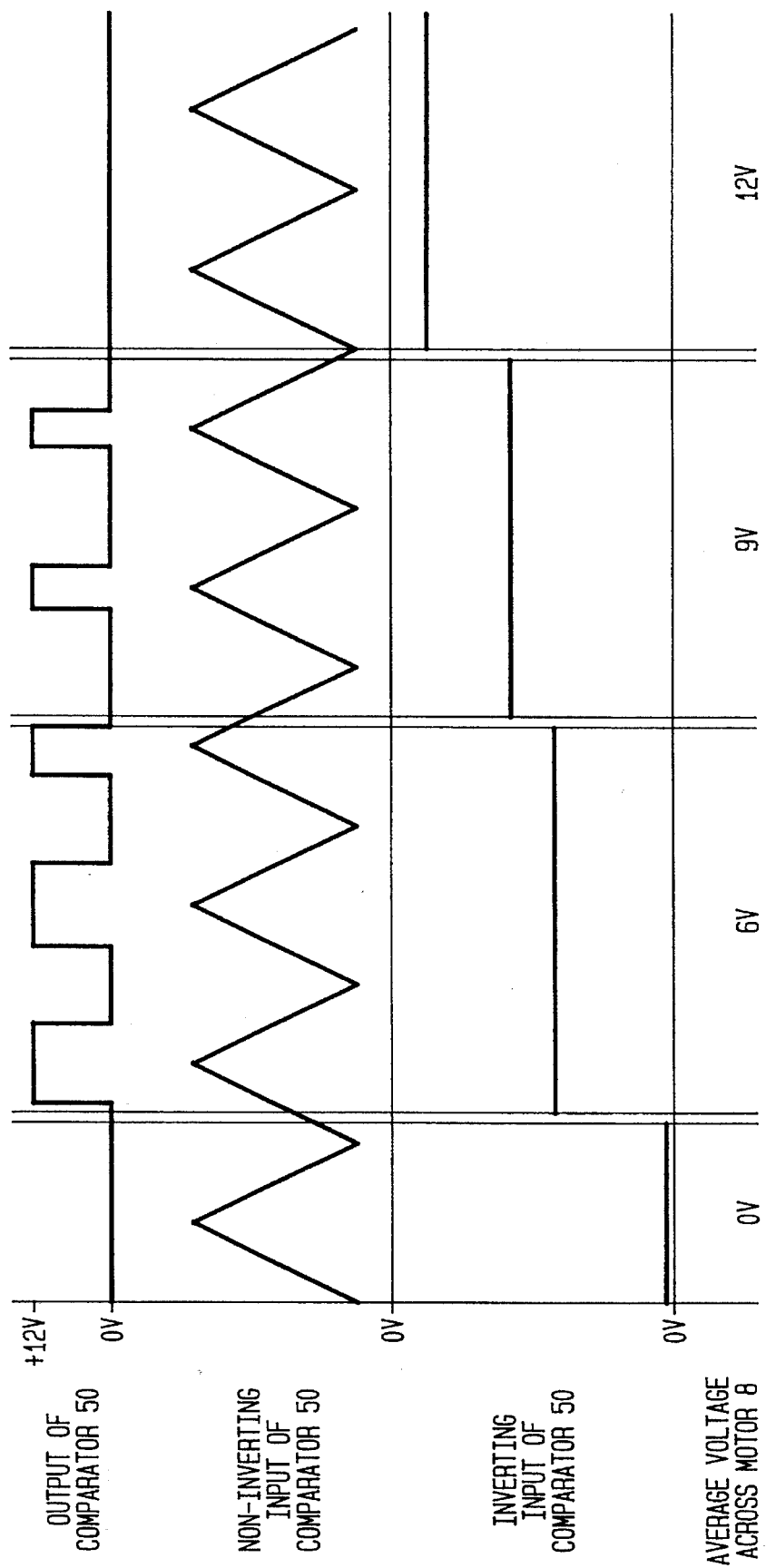
FIG. 3 is a signal timing diagram showing how pulse-width modulated signals are generated in the preferred embodiment of the invention.

To produce this pulse-width modulated signal, the comparator 50 compares two input signals (see FIG. 3). One of these input signals—the one present at the non-inverting input of the comparator 50—is a 25 kHz sawtooth wave produced by integrating the 25 kHz clock signal which is present at the input 34. This integration is carried out by an integrator composed of a resistor 52 and a capacitor 54; the capacitor 54 is connected between the non-inverting input of the comparator 50 and ground, and the resistor 52 is connected in series between the input 34 and the capacitor 54. The other input signal—the one produced at the output of an operational amplifier 56 and present at the inverting input of the comparator 50—is an error signal which reflects any difference between the desired current through the motor 8 and the actual current through the motor 8. (The operational amplifier 56 is part of a second feedback loop which controls the current through the motor 8; the error signal produced by the first feedback is input to the second feedback loop.)

It will be recalled that the error signal at the output of operational amplifier 42 reflects the difference, if any, between the command voltage C and the EMF generated by the operation of the motor 8. This error signal is routed to the non-inverting input of the operational amplifier 56 through a voltage divider composed of a resistor 58 (which is connected between the non-inverting input and ground) and a resistor 60 (which is connected between the ungrounded end of the resistor 58 and the output of the operational amplifier 42). The inverting input of the operational amplifier 56 is connected to a resistor 62, which in turn is connected to the common junction point of the resistors 36 and 38 and which therefore receives a voltage which represents the current through the motor 8. The operational amplifier 56 amplifies the difference between these two input signals and the output of the operational amplifier 56 controls the duty cycle of the motor 8. In this way, the current through the motor 8 is controlled by the output of the operational amplifier 42.

To summarize and recapitulate, when the control circuit 14 is operated in the neonatal mode, the clock signal at the input 34 is integrated, pulse-width-modulated in the comparator 50, and used to control the duty cycle of the FET 48. This in turn varies the voltage across the motor 8 and therefore the current through the motor 8. As the speed of the motor 8 starts to vary (because of changes in load on the pump) the EMF generated within the motor 8 varies from the control voltage C and the variation results in a positive or negative voltage at the output of the operational amplifier 42 (which is a part of the first, or motor speed control, feedback loop). The operational amplifier 56 will then change the pulse-width modulation of the output of the comparator 50 and suitably control the current through the motor 8 by varying the duty cycle of the FET 48 so as to restore proper speed of the motor 8; increased current though the motor 8 causes the torque of the motor 8 to increase and accelerates the motor 8; decreased current has the opposite effect. The command input to the second (motor current control) feedback loop (i.e. the voltage at the non-inverting input of the operational amplifier 56) is limited by the power supply voltage to operational amplifier 42 and the voltage divider formed by the resistors 58 and 60. By limiting this command voltage the second (motor current control) feedback loop formed by the operational amplifier 56 limits the current through the motor 8 at motor startup or under fault conditions.

In the "adult" mode, i.e. with a logically high signal present at the input 32, the motor 8 is driven at its maximum speed because the command voltage C is increased to a level which would cause the EMF of the source S to be greater than the DC supply voltage. This causes the output of the operational amplifier 42 to be forced to its maximum voltage. The increase comes about because the input 32 is connected to the non-inverting input of the operational amplifier 42 via a resistor 39. In this mode, the FET 48 only turns off when the current through the motor 8 increases to the point where the voltage at the inverting input of the operational amplifier 56 is greater than the voltage at the non-inverting input. Thus, in the "adult" mode, the control circuit 14 causes the motor 8 to operate at maximum speed and the output of the operational amplifier 42 is maintained at a logically high value. Consequently, when the control circuit 14 is operated in the "adult" mode, the only condition which induces a change in the duty cycle of the FET 48 is an overcurrent condition, i.e. an excessive current draw of the motor 8.

Because the FET 48 is turned on and off and the motor 8 has a relatively high inductance, it is necessary to provide an electrical connection between both terminals of the motor 8 to permit continuous current flow. This is accomplished by use of Schottky diode 64, which has a grounded anode and a cathode connected to the ungrounded side of the motor 8. When the FET 48 is turned off and the motor 8 is not dynamically braked (see below), the diode 64 makes it possible for the motor current to continue flowing due to the energy stored in the inductors of the motor 8. To prevent brush noise and arcing within the motor 8 from affecting the rest of the circuit, the ungrounded side of the motor 8 is grounded via a high pass filter made up of a capacitor 66 and a resistor 68 which is in series therewith.

A low-pass filter (composed of a parallel network in which a capacitor 70 bridges across a series-connected network of a capacitor 72 and a resistor 74) is connected between the output and the inverting input of the operational amplifier 42. This smooths the switching voltage across the motor 8 so that the feedback loop responds to average values rather than instantaneous ones. Similarly, another low pass filter (this one composed of a parallel network in which a capacitor 76 bridges across a series-connected network of a capacitor 78 and a resistor 80) is connected between the output and the inverting input of the operational amplifier 56. This eliminates ripple from the output of the operational amplifier 56 so that the duty cycle at the output of the comparator 50 is inversely proportional to the average voltage at the output of the operational amplifier 56.

The above description has focussed on the operation of the motor 8 when the motor 8 is turned on. In this instance, the FET 48 is turned on and off. However, in accordance with the preferred embodiment, the motor 8 is dynamically braked, i.e. is shorted over a low-resistance path; this involves operation of the N-channel FET 82.

To understand the operation of the FET 82, the operation of the control circuit 14 will be described on the assumption that the motor 8 is first turned on from an initial off state and is subsequently turned off from that on state (i.e. that the input 30, initially low, is first brought logically high and later brought logically low once more).

The input 30 is connected via a voltage divider to the base of the transistor 84. The collector of the transistor is connected to one end of a resistor 86; the other end of the resistor 86 is connected to the positive supply. One end of a resistor 88 is connected to the common junction point between the collector of the transistor 84 and the low end of the resistor 86, and the other end of the resistor 88 is connected to the common junction point of the resistor 46 and the capacitor 70. Therefore, the resistors 86, 88 and 46 form a voltage divider having a tap to which the collector of the transistor 84 is connected. When the transistor 84 is off, this tap is logically high.

The inverting input of the operational amplifier 42 is connected to this tap via resistor 88 and the inverting input of the operational amplifier 56 is connected to this tap via resistor 90. When the tap is logically high, the outputs of the operational amplifiers 42 and 56 are forced logically low. This causes the output of the comparator 50 to be logically high, turning off the FET 48 and insuring that no current is supplied to the motor 8.

This tap is also connected to the non-inverting input of a comparator 92, and the output of the comparator 92 is connected to the gate of the FET 82. When the tap is logically high, the output of the comparator 92 is likewise high and the source-drain path of the FET 82 is turned on, causing the motor 8 to be shorted via a low resistance path.

Thus, because the input 30 is initially logically low, the outputs of the operational amplifiers 42 and 56 are initially logically low, the outputs of the comparators 50 and 92 are logically high, the FET 48 is turned off, and the FET 82 is turned on.

When the input 30 is brought logically high to turn the motor 8 on, the transistor 84 is turned on and the voltage at the collector of the transistor 84 drops. This causes the output of the comparator 92 to become logically low and makes the source-drain path of the FET 82 nonconductive, removing the low-resistance short across the motor 8. At the same time, the voltages at the outputs of the operational amplifiers 42 and 56 begin to rise in accordance with the time constants of the low-pass filters which are respectively associated with them. Once the voltages at the outputs of the operational amplifiers 42 and 56 become sufficiently high, the comparator 50 begins to produce a pulse-width modulated signal at its output, the duty cycle of the FET 48 is appropriately regulated and the speed of the motor 8 is appropriately controlled as described above.

The base of a transistor 94 is connected to the output of the comparator 50 via a resistor 96. The emitter of the transistor 94 is connected to the source and the collector is connected to the ungrounded end of a capacitor 98. The other end of the capacitor 98 is grounded. A voltage divider composed of two series connected resistor 100 and 102 is connected across the capacitor 98, and the tap of this voltage divider is connected to the inverting input of the comparator 92.

As a pulse-width modulated signal appears at the output of the comparator 50 and the motor 8 operates, the base of the transistor 94 is brought low and high and the transistor 94 is consequently turned on and off. The current through the transistor 94 charges the capacitor 98 relatively quickly. The capacitor 98 remains fully charged while the pulse-width modulated signal is produced at the output of the comparator 50 because it discharges only relatively slowly through resistors 100 and 102 and the charge on its plates is refreshed whenever the transistor 94 turns on. As a result, the inverting input of the comparator 92 remains logically high, the output of the comparator 92 remains logically low, and the source-drain path of the FET 82 is kept in a nonconductive state.

When the motor 8 is to be turned off from a turned-on state, the voltage at the input 30 drops from a logically high state to a logically low state. This causes the inverting inputs of the operational amplifiers 42 and 56 to become logically high, thereby causing the output of the comparator 50 to become low, causing the source-drain path of the FET 48 to become nonconductive and cutting off the supply of electrical power to the motor 8. For some time, the motor 8 continues to turn. During this time, the capacitor 98 discharges; the lack of a logically high signal at the output of the operational amplifier 50 keeps the transistor 94 turned off and there is no current to replenish the charge across the capacitor 98 (which discharges through the resistors 100 and 102).

Some time later, the discharge of the capacitor 98 has continued such that the voltage at the inverting input of the comparator 92 becomes less than the voltage at the non-inverting input of the comparator 92. The output of the comparator 92 then becomes logically high. This brings the gate of the FET 82 high.

The source-drain path of the FET 82 is connected between the ungrounded side of the motor 8 and the ungrounded end of the resistor 36. As a result, when the FET 82 is turned on by application of a logically high signal to its gate, the motor 8 is shunted over a low resistance path. The EMF then causes a reverse current to flow in the motor 8, generating a torque that quickly halts rotation of the shaft of the motor 8.

To summarize, when the motor 8 is to be turned on after having been turned off, the first thing that happens is that the FET 82 becomes nonconductive. (This is done to prevent the source 16 from being shorted to ground.) Next, the feedback loop which includes the operational amplifiers 42 and 56 and the comparator 50 begins to operate and to control the speed of the motor 8 to the speed desired.

When the motor 8 is to be turned off after having been turned on, the first thing that happens is that the feedback loop is shut down by driving the outputs of the operational amplifiers 42 and 56 low. Next, the motor 8 continues to run without external power, the current generated by the motor 8 being routed through the diode 64. Finally, the state of discharge of the capacitor 98 progresses until the source-drain path of the FET 82 becomes conductive, thereby dynamically braking the motor 8 by shorting it across a low-resistance path.

The inverting input of the comparator 92 is connected to the positive supply via a resistor 104 and the non-inverting input of the comparator 50 is connected to the positive supply via a resistor 106. This serves to provide a positive reference voltage for the comparator 92. This provides a means of driving the output of the comparator 92 high if the source (not shown) of the 25 kHz clock signal ceases to function.

Although a preferred embodiment has been described above, the scope of the invention is limited only by the following claims:

I claim:

1. An automatic blood pressure monitor, comprising:
    an inflation cuff;
    a pump connected to the cuff for inflating the cuff with air when operated;
    a DC motor operatively connected to the pump; and
    a speed control circuit operatively connected to the motor, for causing the motor to selectively operate at one of a first and second, lower, speed, and thereby causing said pump to selectively operate at one of a first and second, lower, flow rate, respectively, the speed control circuit including a feedback type control loop having a feedback input responsive to a signal representative of the actual speed of the motor, and a control input responsive to a signal representative of a desired motor speed, for regulating the speed of the motor at at least one of said first and second speeds so that said regulated speed is substantially constant independent of load on said motor.

2. The blood pressure monitor of claim 1, wherein the speed control circuit includes means for limiting motor current.

3. The blood pressure monitor of claim 1, wherein the speed control circuit includes means for electrically braking the motor.

4. The blood pressure monitor of claim 3, wherein said braking means brakes the motor after a time delay period which commences after motor power is cut off.

5. The blood pressure monitor of claim 1, wherein said pump is of a triple-diaphragm design.

6. The blood pressure monitor of claim 1, wherein said feedback input is responsive to an EMF induced voltage produced by said motor.

7. The blood pressure monitor of claim 1, wherein said regulated speed is said second, lower, speed.

8. The blood pressure monitor of claim 1, wherein said speed control circuit includes a comparator having a first input responsive to the signal representative of the actual speed of the motor, a second input responsive to the signal representative of the desired speed of said motor, and an output for providing an output signal which is applied for regulating the speed of said motor so that it is substantially constant independent of load on said motor.

\* \* \* \* \*